US010830772B2

(12) United States Patent
Lettieri et al.

(10) Patent No.: US 10,830,772 B2
(45) Date of Patent: Nov. 10, 2020

(54) DETECTION METHOD AND KIT

(71) Applicant: The European Union, represented by the European Commission, Brussels (BE)

(72) Inventors: Teresa Lettieri, Gavirate (IT); Valentina Elisabetta Viviana Ferrero, Turin (IT)

(73) Assignee: THE EUROPEAN UNION, REPRESENTED BY THE EUROPEAN COMMISSION, Brussels (BE)

(*) Notice: Subject to any disclaimer, the term of this patent is extended or adjusted under 35 U.S.C. 154(b) by 124 days.

(21) Appl. No.: 15/556,148

(22) PCT Filed: Mar. 3, 2016

(86) PCT No.: PCT/EP2016/054497
§ 371 (c)(1),
(2) Date: Sep. 6, 2017

(87) PCT Pub. No.: WO2016/142252
PCT Pub. Date: Sep. 15, 2016

(65) Prior Publication Data
US 2018/0045731 A1 Feb. 15, 2018

(30) Foreign Application Priority Data
Mar. 6, 2015 (EP) .................................... 15158044

(51) Int. Cl.
*G01N 33/58* (2006.01)
*G01N 33/68* (2006.01)

(52) U.S. Cl.
CPC ....... *G01N 33/582* (2013.01); *G01N 33/6872* (2013.01); *G01N 2333/705* (2013.01); *G01N 2500/00* (2013.01)

(58) Field of Classification Search
CPC .................................................. G01N 33/582
See application file for complete search history.

(56) References Cited

FOREIGN PATENT DOCUMENTS

WO          97/30353        8/1997

OTHER PUBLICATIONS

Andreasen et al. ("The Zebrafish (*Danio rerio*) Aryl Hydrocrbon Receptor Type 1 Is a Novel Vertebrate Receptor" Molecular Pharamacology, vol. 62, No. 2, pp. 234-249, 2002) (Year: 2002).*
Jonsson et al. ("The tryptophan photoproduct 6-formylindolo[3,2-b]carbazole (FICZ) binds multiple AhRs and induces multiple CYP1 genes via AHR2 in zebrafish", Chemico-Biological Interactions, vol. 181, pp. 447-454, published Jul. 15, 2009. (Year: 2009).*
Tholander J et al., "Syntheses of 6, 12-Disubstituted 5,11-Dihydroindolo [3,2-b] carbazoles, Including 5,11-Dihydroindolo [3,2-b] carbazole-6,12-dicarbaldehyde, an Extremely Efficient Ligand for the TCDD (Ah) Receptor" , Tetrahedron, Elsevier Science Publishers, Amsterdam, NL, vol. 55, No. 43, Oct. 22, 1999 (Oct. 22, 1999) , pp. 12577-12594, XP004179346, ISSN: 0040-4020, DOI: 10.1016/S0040-4020(99)00733-4.
Wang et al., "Synthesis of a ligand-quencher conjugate for the ligand binding study of the aryl hydrocarbon receptor using a FRET assay.", Medicinal Chemistry Research, vol. 21, 2012, pp. 711-721, XP002757112, DOI: 10.1007/ s00044-011-9575-7.

* cited by examiner

*Primary Examiner* — Tracy Vivlemore
*Assistant Examiner* — Nam P Nguyen
(74) *Attorney, Agent, or Firm* — Lex IP Meister, PLLC

(57) ABSTRACT

Uses of ethyl 5,11-dihydroindolo[3,2-b]carbazole-6-carboxylate as a fluorescent ligand probe, preferably in a binding assay for quantitative analysis in combination with a recombinant aryl hydrocarbon receptor (AhR) protein. A method for detection or quantitative analysis of suspected aryl hydrocarbon receptor (AhR) ligands in a sample, the method comprising the steps of: (a) providing a sample possibly containing at least one known or unknown AhR ligand; (b) mixing said sample with a composition comprising a recombinant AhR protein bound to ethyl 5,11-dihydroindolo[3,2-b]carbazole-6-carboxylate; and (c) determining the presence or the total amount of said at least one known or unknown AhR ligand in the sample by fluorescence spectroscopy. Use e.g. for screening of unknown compounds to determine their binding ability to AhR; for analyzing unknown chemical mixtures to assess the presence of ligands able to bind to AhR; for screening of Polycyclic Aromatic Hydrocarbon (PAHs) from water, food or sediment; for screening of PAHs or dioxin-like compounds in water, food or sediment; for testing for pollutant removal in water and waste water treatment plants; for testing for water reuse; for testing the presence of dioxin-like compounds in incinerator plants; or for testing of bodily fluids of humans or animals exposed to PAHs or dioxin-like compounds.

8 Claims, 1 Drawing Sheet

DETECTION METHOD AND KIT

TECHNICAL FIELD

The present invention generally relates to assessing exposure to pollutants present in complex matrices such as water, food and soil. Furthermore the invention could be useful in the screening for molecules in drug discovery programs.

BACKGROUND ART

The Aryl Hydrocarbon Receptor (AhR) is a protein, which is bound and activated by a wide range of chemicals including synthetic and environmental chemicals, dietary and endogenous molecules. It is a chemical/xenobiotic-dependent intracellular receptor that is able to stimulate gene transcription as a response to a particular physiological situation.

The interest for this receptor has increased over the last years. Many molecules have been shown to bind and exert their effects through the AhR such as polycyclic aromatic hydrocarbons (PAHs), which are worldwide present pollutants. The toxicity of dioxin TCDD (one of the most potent non-genotoxic tumor-promoting substances known) is almost exclusively mediated via this receptor.

Also, although the precise role of AhR is still unknown, recent studies suggest a role in tumor development. The AhR can bind several molecules and these can act either as agonist exerting their toxicity through the second messenger signal, or as antagonist, blocking any activity. For example, molecules such as pigments in green and black tea have antagonist activity, which seems to be at the basis of their antioxidant function (blocking AhR activity in tumor genesis).

The aryl hydrocarbon receptor (AhR) is a ligand-dependent transcription factor that mediates many of the biological and toxicological actions of a variety of hydrophobic natural and synthetic chemicals.

Although there are a few commercial kits currently available to measure the binding to the AhR in vitro, they are either based on immune assay (Ah Immunoassay® kit), on cell culture (Tebu-Bio), or on radiolabelled molecules:

- The Ah Immunoassay® kit, Biosense Laboratories, is complicated to use and is relatively expensive due to the use of antibodies and specific additional proteins.
- The Tebu-Bio PXR allows for quantification of receptor activation in cells by using stable human 1A2-DRE cell line harboring a specific AhR-regulated reporter gene with a CYP1A2 promoter. In this case the system requires cell culture expertise which is not common to all laboratories. In addition, cell culturing is a time consuming and expensive technique.
- The radiolabelling methods are based on radiolabeled ligand such as [$^3$H]dioxin or [$^{125}$I]dioxin that allow competition by low-affinity ligands (Phelan D, Winter G M, Rogers W J, Lam J C, and Denison M S, 1998, Activation of the Ah receptor signal transduction pathway by bilirubin and biliverdin. Arch Biochem Biophys 357: 155-163). These techniques require facilities and staff equipped and trained to handle radioactive compounds, which is not common. In addition, dioxins are tumorigenic compounds.

Hence, the existing solutions use expensive antibodies, are not sufficiently sensitive or make use of toxic or radioactive chemicals, thus rendering the assays time-consuming, technically cumbersome and expensive.

Technical Problem

It is an object of the present invention to provide an assay for the Aryl Hydrocarbon Receptor (AhR) binding activity which is simple to use, sensitive and delivers fast results.

General Description of the Invention

In order to overcome at least some of the above-mentioned problems and to provide a solution to the above object, the present invention proposes in a first aspect the use of ethyl 5,11-dihydroindolo[3,2-b]carbazole-6-carboxylate as a fluorescent ligand probe, preferably in a binding assay for quantitative analysis. In a particularly preferred aspect, the invention envisages the use of ethyl 5,11-dihydroindolo[3,2-b]carbazole-6-carboxylate as a fluorescent ligand probe in combination with a recombinant aryl hydrocarbon receptor (AhR) protein, especially in a competitive binding assay.

Indeed, the present inventors have found that ethyl 5,11-dihydroindolo[3,2-b]carbazole-6-carboxylate exhibits a fluorescence signal with a significantly different emission spectrum in hydrophilic environment compared to its spectrum in hydrophobic conditions. In fact, when excited at 280 nm, ethyl 5,11-dihydroindolo[3,2-b]carbazole-6-carboxylate shows emission peaks at 328 nm and 450 nm in hydrophobic organic solvent, whereas when excited at 280 nm when in hydrophilic environment, it only emits at 330 nm.

The inventors also found that ethyl 5,11-dihydroindolo[3,2-b]carbazole-6-carboxylate exhibits a binding ability to AhR which was appropriate for binding assays, especially in the form of competitive binding assays with common AhR ligands, such as known toxic compounds and pollutants. Indeed, ethyl 5,11-dihydroindolo[3,2-b]carbazole-6-carboxylate showed a binding affinity that is high enough to allow the competition of other compounds to the receptor, yet not too high, because this would cause the inability of ethyl 5,11-dihydroindolo[3,2-b]carbazole-6-carboxylate to be displaced from the AhR (and thus not modify the fluorescence in the presence of such compounds). Indeed, it has been ascertained that the addition of ethyl 5,11-dihydroindolo[3,2-b]carbazole-6-carboxylate to AhR causes the appearance of an emission peak with a maximum at about 450 nm±10 nm, which is due to its binding into the active site of AhR (lipophilic environment). The presence and the intensity of this emission peak allows to qualitatively and more importantly quantitatively measure the binding of ethyl 5,11-dihydroindolo[3,2-b]carbazole-6-carboxylate to appropriate proteins, such as AhR proteins and especially recombinant AhR proteins.

In a still further aspect, the present invention therefore provides a method for detection or quantitative analysis of suspected aryl hydrocarbon receptor (AhR) ligands in a sample, the method comprising the steps of:

(a) providing a sample possibly containing at least one known or unknown AhR ligand;

(b) mixing said sample with a composition comprising a recombinant AhR protein already bound to or able/ready to bind to ethyl 5,11-dihydroindolo[3,2-b]carbazole-6-carboxylate; and (c) determining the presence or the total amount of said at least one known or unknown AhR ligand in the sample by fluorescence spectroscopy.

Such a method thus allows to determine the presence or even the amount of compounds competing with ethyl 5,11-dihydroindolo[3,2-b]carbazole-6-carboxylate on the AhR binding site in a competitive binding assay by measuring the emission peak at about 450 nm±10 nm. It is to be noted that in step (b) ethyl 5,11-dihydroindolo[3,2-b]carbazole-6-carboxylate is preferably already bound to the AhR protein, alternatively both compounds are ready or able to bind, which means in the present context that they may be added separately during mixing. In the absence of competing molecules, the peak is maximum, while increasing amounts of competing compounds will correspondingly reduce the presence of ethyl 5,11-dihydroindolo[3,2-b]carbazole-6-carboxylate in the relevant site of the AhR and thereby decrease the emission intensity at said wave length. The intensity of the emission peak at around 450 nm may thus be successfully used for the detection or even the quantitative analysis of suspected AhR ligands in a sample.

In a preferred embodiment of the method, the recombinant AhR protein is a 600 amino acid recombinant protein encoded by an AhR isoform from zebrafish, preferably an AhR2 isoform. In particular, said AhR isoform may be obtained by expression in *E. coli* of the gene encoding the sequence of an AhR isoform from zebrafish.

In a still further preferred embodiment of the present method, the fluorescence spectroscopy is polarized fluorescence spectroscopy.

As has been mentioned in the introduction, known methods for the detection or quantitative analysis of suspected aryl hydrocarbon receptor (AhR) ligands in a sample are time-consuming, technically cumbersome and expensive. As can be appreciated, the method of the present invention is none of those. It is fast compared to previous methods: steps (b) and (c) are accomplished within 6 hours or less, preferably within 3 hours or even less. It is technically easy: it basically only requires mixing the reagents with the sample, a certain incubation time to allow for any competitive displacement of ethyl 5,11-dihydroindolo[3,2-b]carbazole-6-carboxylate from the AhR protein and the measuring of the 455 nm peak with existing and common fluorescence equipment. Finally it is not expensive compared to the known method as it does neither require special equipment, nor many reagents. Preferably, in the present method, the fluorescence spectroscopy is differentiated based on emission spectrum in hydrophilic environment versus its spectrum in hydrophobic conditions.

As a further aspect, the invention therefore provides a kit for detection or quantitative analysis of suspected aryl hydrocarbon receptor ligands in a sample, the kit comprising a recombinant AhR protein and ethyl 5,11-dihydroindolo[3,2-b]carbazole-6-carboxylate, either separately in two compositions or preferably bound a in a single composition. Preferably the recombinant AhR protein is a 600 amino acid recombinant protein encoded by an AhR isoform from zebrafish, preferably obtained by expression in *E. coli* of the gene encoding the sequence of an AhR isoform from zebrafish.

The invention may be useful for many applications or uses. Therefore, in a still further aspect, the invention also considers the use of a method or a kit as described herein for screening of unknown compounds to determine their binding ability to AhR; e.g. for analyzing unknown chemical mixtures to assess the presence of ligands able to bind to AhR; for screening of Polycyclic Aromatic Hydrocarbon (PAHs) from water, food or sediment; for screening of PAHs or dioxin-like compounds in water, food or sediment; for testing for pollutant removal in water and waste water treatment plants; for testing for water reuse; for testing the presence of dioxin-like compounds in incinerator plants; or for testing of bodily fluids of humans or animals exposed to PAHs or dioxin-like compounds. These uses are only examples of what can be determined by putting the present invention into practice. Other uses and application are of course also covered if they are within the scope of the present claims.

BRIEF DESCRIPTION OF THE DRAWINGS

Preferred embodiments of the invention will now be described, by way of example, with reference to the accompanying drawings in which.

Further details and advantages of the present invention will be apparent from the following detailed description of non-limiting embodiments with reference to the attached drawings.

DESCRIPTION OF PREFERRED EMBODIMENTS

The inventors expressed the encoding gene sequence for the AhR2 from zebrafish in *Escherichia coli* cells to produce the high yield of a 600 amino acid recombinant protein. The protein was purified by using Histidine tag affinity column. The protocol used allowed to obtain a good yield of pure protein that is correctly folded.

Figure 1:
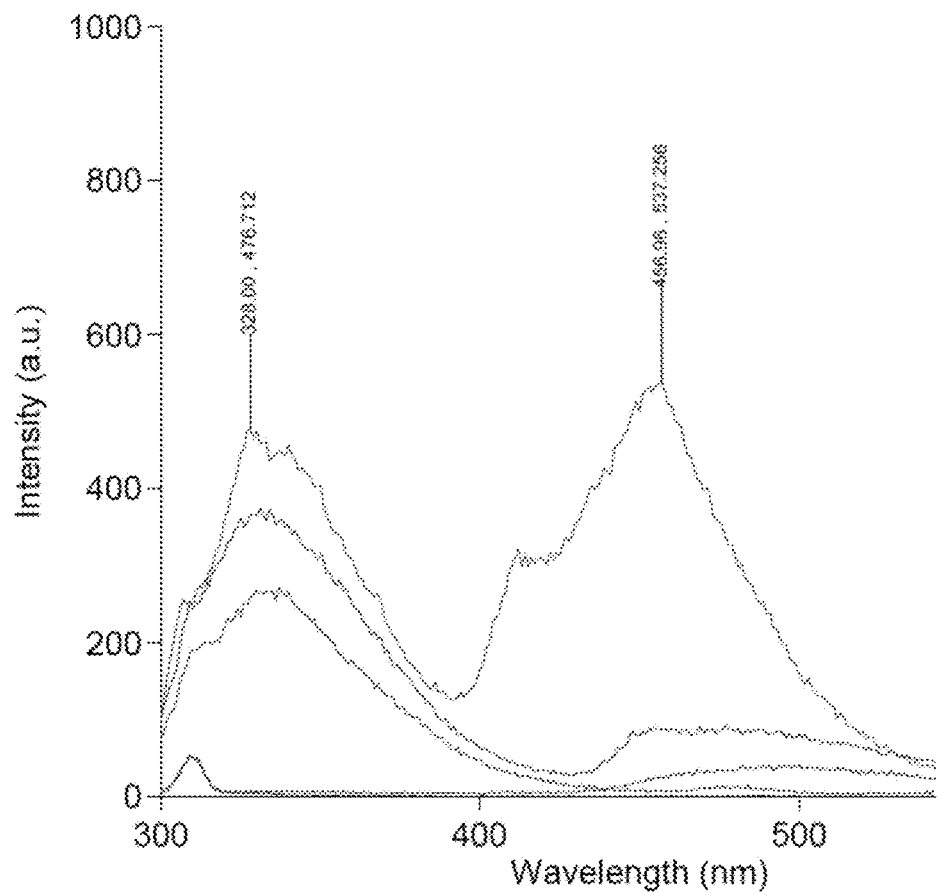
FIG. 1 is a graph showing the intensity (arbitrary units) as a function of the wave length (nm) obtained in a fluorescence spectroscopy assay according to the invention.

The inventors developed an assay for the Aryl Hydrocarbon Receptor binding activity as an alternative to known methods and investigated which molecules are the most suitable for building a competitive binding assay as in vitro ligands, and to make these molecules fluorescent or more fluorescent. The inventors found that ethyl 5,11-dihydroindolo[3,2-b]carbazole-6-carboxylate is a high fluorescence emittant in hydrophobic organic solvent (FIG. 1, top line at 328 nm) when excited at 280 nm, showing emission peaks at 328 and 456 nm. The same concentration of ethyl 5,11-dihydroindolo[3,2-b]carbazole-6-carboxylate in aqueous buffer environment has a very low fluorescence signal (FIG. 1, bottom line at 328 nm). The AhR protein in buffer environment (FIG. 1, second line from the bottom at 328 nm), when excited at 280 nm, is only emitting at about 330 nm; the addition of ethyl 5,11-dihydroindolo[3,2-b]carbazole-6-carboxylate to the AhR (FIG. 1, second line from the top at 328 nm), always at the same concentrations, causes the appearance of an emission peak with maximum at 450 nm, that is due to the binding of ethyl 5,11-dihydroindolo[3,2-b]carbazole-6-carboxylate into the active site of AhR. Indeed if ethyl 5,11-dihydroindolo[3,2-b]carbazole-6-carboxylate is a ligand of AhR it moves from an aqueous environment (buffer) to a more hydrophobic environment (hydrophobic internal binding site of the AhR receptor), causing the increase in fluorescence emission at 450 nm.

Competition Assay

To confirm that ethyl 5,11-dihydroindolo[3,2-b]carbazole-6-carboxylate was really binding inside the active site of AhR, further investigations were performed. The inventors tested if they could observe a decrease of the signal at 450 nm by adding known ligands as competitor molecules to displace the ethyl 5,11-dihydroindolo[3,2-b]carbazole-6-carboxylate. Only if ethyl 5,11-dihydroindolo[3,2-b]carbazole-6-carboxylate is bound in the active site it should be displaced in a linear manner from the AhR. Increasing concentrations of four different competitors were added to the pre-incubated solution of AhR+ethyl 5,11-dihydroindolo [3,2-b]carbazole-6-carboxylate, showing in all cases a decrease of the 450 nm peak at increasing concentrations of competitor. The additions were done every 10 minutes. The assay shows a linear response in the range 0-0.2 µM (0-200 nM). We can quantify the presence of this competitor in this range of concentration. At higher concentrations of competitor the signal doesn't drop down anymore, meaning that all the 5,11-dihydroindolo[3,2-b]carbazole-6-carboxylate has been displaced from the active site of AhR. The competitor was added in a very small volume not to have variations of signal due to the changed total volume of reaction. Control samples with only buffer and solvent used for dissolving the competitor were also prepared, to demonstrate that the decrease of the intensity of the peak at 450 nm is not due to solvent effect.

Figure 2:
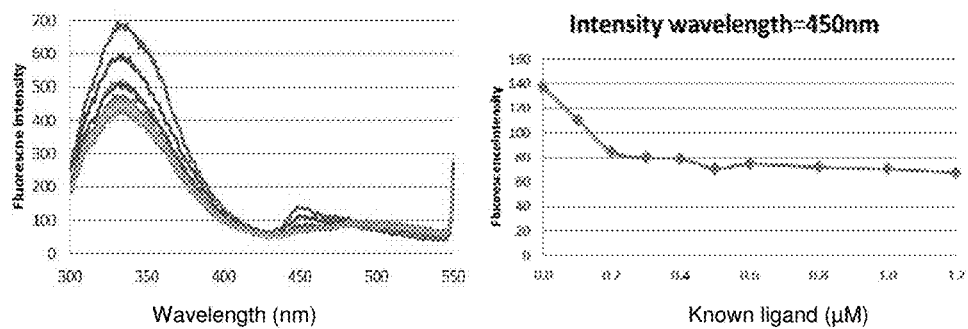
FIG. 2 is double graph showing in the left panel the fluorescence emission spectra of a pre-incubated solution of AhR+ethyl 5,11-dihydroindolo[3,2-b]carbazole-6-carboxylate and serial additions of a known competing ligand. In the right panel, the intensity of the peak at 450 nm is shown at increasing concentrations of the known ligand.

In FIG. 2 are reported the fluorescence emission spectra of pre-incubated solution of AhR+ethyl 5,11-dihydroindolo [3,2-b]carbazole-6-carboxylate and serial additions of a known ligand of AhR.

FIG. 2: Left panel—fluorescence emission spectra of pre-incubated solution of AhR+ethyl 5,11-dihydroindolo[3,2-b]carbazole-6-carboxylate (top spectrum at 450 nm) and serial additions of the known ligand. Right panel—the intensity of the peak at 450 nm is followed at increasing concentrations of the known ligand.

These results show that ethyl 5,11-dihydroindolo[3,2-b] carbazole-6-carboxylate can be successfully used in qualitative and quantitative detection using fluorescence spectroscopy, especially in combination with AhR protein for the detection and measurement of AhR ligands which are among others important agents as concerns pollution and toxicity.

The invention claimed is:

1. A method for detection or quantitative analysis of suspected aryl hydrocarbon receptor (AhR) ligands in a sample, the method comprising the steps of:
    (a) providing a sample possibly containing at least one known or unknown AhR ligand;
    (b) mixing said sample with a composition comprising a recombinant AhR protein capable of binding to the at least one known or unknown AhR ligand, wherein the recombinant AhR protein is bound to ethyl 5,11-dihydroindolo[3,2-b]carbazole-6-carboxylate; and
    (c) determining the presence or the total amount of said at least one known or unknown AhR ligand in the sample by fluorescence spectroscopy.

2. The method according to claim 1, wherein the determination in step (c) is made based on the measurement of emission peak intensity at a wave length of 450 nm±10 nm.

3. The method according to claim 1, wherein the recombinant AhR protein is a 600 amino acid recombinant protein encoded by an AhR isoform from zebrafish.

4. The method according to claim 1, wherein fluorescence spectroscopy is polarized fluorescence spectroscopy.

5. The method according to claim 1, wherein steps (b) and (c) are accomplished within 6 hours or less.

6. The method according to claim 1, wherein fluorescence spectroscopy is differentiated based on emission spectrum in hydrophilic environment versus its spectrum in hydrophobic conditions.

7. The method according to claim 3, wherein the recombinant AhR protein is obtained by expression in *E. coli* of the gene encoding the sequence of a AhR isoform from zebrafish.

8. The method according to claim 5, wherein steps (b) and (c) are accomplished within 3 hours or less.

* * * * *